(12) United States Patent
Shipov et al.

(10) Patent No.: US 7,410,655 B2
(45) Date of Patent: Aug. 12, 2008

(54) ANTICANCER AGENT

(75) Inventors: Valery Pavlovich Shipov, Saint Petersburg (RU); Valery Afanasievich Trofimov, deceased, late of Saint-Petersburg (RU); by Nadezhda Vasilievna Trofimova, legal representative, Saint-Petersburg (RU); Evgeny Sergeevich Pigarev, Saint-Petersburg (RU); Aleksandr Ivanovich Popov, Saint-Petersburg (RU); Viktor Nikolaevich Ivanov, Saint-Petersburg (RU)

(73) Assignee: Nobel Limited Liability Company, Saint Petersburg (RU)

( * ) Notice: Subject to any disclaimer, the term of this patent is extended or adjusted under 35 U.S.C. 154(b) by 107 days.

(21) Appl. No.: 10/468,724

(22) PCT Filed: Feb. 20, 2002

(86) PCT No.: PCT/RU02/00061

§ 371 (c)(1),
(2), (4) Date: Feb. 17, 2004

(87) PCT Pub. No.: WO02/66039

PCT Pub. Date: Mar. 29, 2002

(65) Prior Publication Data

US 2005/0080069 A1    Apr. 14, 2005

(30) Foreign Application Priority Data

Feb. 21, 2001   (RU) .............................. 2001105781

(51) Int. Cl.
*A61K 33/24* (2006.01)
*A61K 35/10* (2006.01)
*A61K 36/00* (2006.01)
*A61K 31/555* (2006.01)
*A61P 35/00* (2006.01)

(52) U.S. Cl. .................. 424/649; 424/725; 514/22; 514/184; 514/492; 514/554; 514/557; 514/708; 514/922

(58) Field of Classification Search .................. 514/22, 514/184, 492, 554, 557, 708, 922; 424/649, 424/725
See application file for complete search history.

(56) References Cited

U.S. PATENT DOCUMENTS

| | | | | |
|---|---|---|---|---|
| 4,278,660 A | * | 7/1981 | Allcock et al. | 424/78.23 |
| 4,565,806 A | * | 1/1986 | Setala | 514/54 |
| 5,998,648 A | * | 12/1999 | Sohn et al. | 556/137 |

OTHER PUBLICATIONS

Derwent Abstract 1998-167679, abstracting RU 2086261 (1997).*
Derwent Abstract 1990-371705, abstracting JP 02268122 (1990).*
FIle JAPIO on STN Online, abstract No. 1990-268122, abstracting JP 02268122 (1990).*
English abstract of RU 2,138,259 (Sep. 1999).*
English abstract of RU 2,131,250 (Jun. 1999).*

* cited by examiner

*Primary Examiner*—John Pak
(74) *Attorney, Agent, or Firm*—WolfBlock LLP

(57) ABSTRACT

An anticancer agent containing platinum preparation, humic substances, water and sodium chloride.

Potassium tetrachloroplatinate is used as a platinum compound and lignohumic acid ammonium salts are used as humic substances taken in the following ratio of components per 1 ml of solution:

| | |
|---|---|
| lignohumic acid ammonium salts | 0.18-0.22 mg |
| potassium tetrachloroplatinate | 0.020-0.040 mg |
| sodium chloride isotonic solution | 0.97-0.99 ml |
| distilled water | up to 1.0 ml |

2 Claims, No Drawings

ANTICANCER AGENT

This application is a 371 of PCT/RU02/00061, filed on Feb. 20, 2002.

FIELD OF THE INVENTION

This invention relates generally to the field of pharmacology and more particularly to anticancer agents containing platinum preparations.

BACKGROUND OF THE INVENTION

Antineoplastic agents that incorporate platinum complexes attract specialists' attention featuring strong anti-tumor action, which causes violation of the mechanism of malignant cells gene action.

Platinum preparations have a wide range of antineoplastic administration. Cis-dichlorodiammineplatinum (DDP), being the most thoroughly investigated agent of this anti-tumor group of agents, is active against tumors of various origins: spontaneous and inoculated ones, as well as those induced by viruses and chemical carcinogens. The DDP major drawback is connected with its high toxicity, which causes malfunction of kidneys, red marrow and the digestive tract.

A certain antineoplastic agent (A, RU 2086261) is known to contain a platinum complex in the form of cis-diaminodichloro-trans-dihydroxyplatinum (IV) (oxoplatinum) at a rate of 10-25% and sodium bicarbonate and sodium alginete—at respective rates of 25-55% and 40-60%. This agent has been designed for oral administration in pills with the total weight of 0.35-0.60 g each. The therapeutic dose of the agent in question has 20 to 150 mg of platinum content. The medicine is active in treatment of a relatively wide range of malignant diseases and can be characterized by inhibition of metastases growth and zero nephrotoxic properties.

Sodium bicarbonate, a component of the medicinal preparation, acts as a loosening agent with respect to the pill. When it gets into the gastric juice acid medium, the juice undergoes neutralization and carbon dioxide evolves. Gastric juice neutralization prevents substitution of oxoplatinum hydroxyl groups for chloro ligands to be accompanied with tetrachloride generation. Resulting in sodium chloride generation, interaction between hydrochloric acid sodium bicarbonate contributes to stabilization of chlorine ions in cis-diaminodichloro-trans-dihydroxyplatinum (IV).

Selection of sodium alginete as a filling agent is connected with its high binding properties and with the fact that alginic acid generated due to its interaction with hydrochloric acid has good compatibility with living tissues.

Thus, oxoplatinum acts as the only effective antineoplastic substance in the agent under consideration, which accounts for the necessity of relatively high dosage concerning its administration and increases the probability of complications associated with the toxicity of platinum preparations.

In the course of research investigation of various platinum complexes on animals and clinical trials of DDP and some of its analogues a variety of biological features characteristic of platinum complexes were discovered: anti-tumor activity and respective side effects. It has been shown that insignificant changes in the molecular structure of the complex are capable of causing drastic changes in the above features with respect to bioactivity, including anti-tumor activity. Existing relationship between the complex structure and its anti-tumor activity encourages the search for new platinum-containing agents featuring both high activity and low toxicity.

SUMMARY AND OBJECTS OF THE INVENTION

The object of the present invention is to create such an anticancer agent which would incorporate platinum compounds of relatively low concentration and bioactive agents, and therefore would ensure both reduced toxicity of the agent and enhanced effectiveness of treatment of malignant diseases.

The set task is solved in such a manner that the medicinal preparation contains additional humic substances and water along with platinum compounds and Na salts, sodium chloride being used as a Na salt.

The proposed anticancer agent is a combined preparation containing both inorganic substances (platinum compounds) and organic bioactive components (humic substances). Platinum compounds feature marked anti-tumor activity.

Acting as the preparation organic components, humic substances represent a large group of natural compounds. Their origin is connected with the hydrolytic decay of wood lignin. Entering into the composition of humic substances, humic acids are active components of some pharmaceuticals related to a biogenic stimulants group (e.g. Humisol, Befungin, and the like).

The sodium chloride aqueous solution ensures isotonicity of the preparation medium with the medium of a living body, which enables intramuscular administration of the agent, for example.

In the course of the research it has been discovered that the complex medicinal preparation containing the platinum preparation and humic substances demonstrates a synergetic increase in activity (shown in an example below).

It is advisable to use lignohumic acid ammonium salts as humic substances and potassium tetrachloroplatinate as a platinum compound; it is expedient to use a Na salt in the form of sodium chloride isotonic solution in the following ratio of components per 1 ml of solution:

| | |
|---|---|
| lignohumic acid ammonium salts | 0.18-0.22 mg |
| potassium tetrachloroplatinate | 0.020-0.040 mg |
| sodium chloride isotonic solution | 0.97-0.99 ml |
| distilled water | up to 1.0 ml |

The ratio of the proposed preparation components was chosen experimentally on grounds of maximum effectiveness under low toxicity conditions.

Platinum content in a therapeutic dose amounts to 0.008-0.0010 mg, being significantly lower than in any of the known medicinal preparations. Therefore, toxic action of the proposed preparation should be many times as low.

It has been experimentally demonstrated that with the decreasing proportion of lignohumic acid salts the preparation effectiveness reduces due to the lower stability of the platinum complex; a therapeutic effect does not intensify with the increasing proportion of lignohumic acid salts. Thus, the upper limit of the lignohumic acid salts content ensures the preparation maximum effectiveness.

A reduction in the potassium tetrachloroplatinate content causes a decrease in the therapeutic effect. Where the potassium tetrachloroplatinate content exceeds the specified amount, the compound stability occurs, toxicity grows and the therapeutic effect decreases.

The sodium chloride solution ensures isotonicity of the preparation medium with the medium of a living body, which enables intramuscular administration of the agent, for example. The amount of the sodium chloride solution is determined on the basis of conformity between the preparation osmotic pressure and the osmotic pressure of blood plasma.

Water is used as a dissolving agent.

The lignohumic acid salts entering into the composition of the proposed agent can be generated by liquid-phase oxidation of hydrolytic lignin with molecular oxygen in the alkaline medium (RU, A, 93037252).

DETAILED DESCRIPTION OF THE INVENTION

The impact mechanism of the proposed anticancer agent is described as follows.

Upon intramuscular administration the agent penetrates into blood and has an effect on hypothalamus, since a rise in endorphins concentration is detected in blood, cerebral tissues and cerebrospinal fluid as early as 20 minutes after the agent administration. Particularly high is the concentration of β-endorphin, a universal homeostasis regulator.

A rise in the β-endorphin concentration in blood causes inhibition of tumor growth due to the impact on certain specific targets of malignant cell membranes. The endorphin increased concentration retains within several hours, resulting in a longer period of impact on the tumor.

In addition, the proposed preparation is capable of inducing the ionophore property, or Kraun effect, which facilitates the permeability of biological membranes to platinum ions. This allows to use relatively low platinum concentration. The same effect ensures penetration of humic substances into the cell, which rapidly accumulate in the tumoral tissue. Having a great number of covalent active bonds, the administered solution reacts with the nucleophilic centers of protein molecules, starting the bifunctional alkylation process in the tumoral tissue nucleic acids. This results in long-term violation of DNA and RNA synthesis, as well as in the blocking of the mitotic cycle and enzyme systems of malignant cells, causing their destruction.

The preparation anti-tumor action was tested on female white rats.

EXAMPLE 1

The PA-23 rhabdomyosarcoma cell suspension was inoculated in the caudal vein of all rats, being generally used as a model for investigating the ability of such preparations to inhibit stroma development, which is characteristic of most malignant tumors.

All the animals were divided into 5 groups. On the following day after the inoculation a physiological solution was intra-abdominal injected into the rats of Group 1 (0.5 ml per animal); 0.1 ml of the preparation—into the rats of Group 2, 0.3 ml of the preparation—into the rats of Group 3; 0.5 ml of the preparation—into the rats of Group 4; and 0.8 ml of the preparation—into the rats of Group 5. Prior to administration the preparation had been diluted with a physiological solution in the ratio of 1 to 10.

Subsequent administration of the preparation (as a placebo control) was carried out every third day. On the 20 th day following the tumoral inoculation the rats were destroyed. Their bodies were dissected, the number of metastases in their lungs calculated and their respective weight determined by means of analytical balance weighing. The Student's t-test was applied to the statistical treatment of the experimental results as shown in Table 1.

TABLE 1

| Metastasizing and metastases growth indicators | Sodium chloride isotonic solution Group 1 (Control) | Anticancer preparation, ml | | | |
|---|---|---|---|---|---|
| | | 0.1 Group 2 | 0.3 Group 3 | 0.5 Group 4 | 0.8 Group 5 |
| Number of rats per group | 19 | 20 | 16 | 17 | 19 |
| Number of metastases | 595 | 616 | 413 | 529 | 579 |
| Average number of metastases per rat | 31.3 ± 6.8 | 30.8 ± 9.3 | 25.8 ± 4.5 | 31.1 ± 9.4 | 30.5 ± 9.5 |
| Average weight of 1 metastasis, mg, | 50.7 ± 2.6 | 37.5 ± 3.1 | 42.8 ± 2.9 | 39.0 ± 3.4 | 37.2 ± 3.3 |
| % of the Control Group | 100 | 74.0 | 84.4 | 76.9 | 73.4 |

The above data indicates that the preparation did not have any effect on the frequency of metastases formation in lungs—their number was virtually equal in all of the groups. At the same time the preparation had a marked impact on the metastases growth—in all pilot groups the average weight of metastases was less than that of the control group and the percentage of the metastases growth inhibition was within the range of 15 to 26%. Thus, the preparation represses the ability of malignant cells to develop stroma with blood vessels, which subsequently results in destruction of the malignant cells themselves.

At the same time an increase in the preparation dosage did not have any essential influence upon the end result.

EXAMPLE 2

As in Example 1, the PA-23 rhabdomyosarcomas were used as a model. Tumoral inoculation was performed in a similar way. The laboratory animals were also divided into groups. The sodium chloride isotonic solution was injected into Group 1 (control), potassium tetrachloroplatinate in the sodium chloride isotonic solution—into Group 2, ammonium lignohumic acid salts in the sodium chloride isotonic solution were injected into Group 3, injections of the proposed preparation diluted with a physiological solution in the ratio of 1 to 10 were given to Group 4. The results are shown in Table 2.

TABLE 2

| Metastasizing and metastases growth indicators | Sodium chloride solution (Control) 0.3 ml | Potassium tetrachloro- platinate solution 0.003 mg/ml | Lignohumic acid salts solution 0.020 mg/ml | Anticancer preparation 0.3 ml |
|---|---|---|---|---|
| Number of rats per group | 16 | 16 | 17 | 18 |
| Number of metastases | 547 | 531 | 539 | 506 |
| Average number of metastases per rat | 34.2 ± 6.4 | 33.2 ± 6.2 | 31.9 ± 6.5 | 28.1 ± 5.6 |
| Average weight of 1 metastasis, mg | 48.5 ± 2.8 | 42.9 ± 4.3 | 37.8 ± 5.2* | 28.4 ± 3.6* |
| % of the Control Group | 100 | 88.5 | 77.9 | 58.6 |

*The difference is significant with respect to the Control Group (probability less than 0.05).

As follows from Table 2, compared to the Control Group, the average weight of 1 metastasis constitutes 58.6% with the proposed preparation applied, whereas these figures constitute 88.5 and 77.9% respectively with the use of its separate components (potassium tetrachloroplatinate and the lignohumic acid salts solution). The figures demonstrate the synergetic effect of the activity related to the preparation components.

Thus, the proposed anticancer agent has a marked antineoplastic action which destroys the mechanism of malignant cells gene action and finally leads to the cells destruction.

What is claimed is:

1. An anticancer agent comprising potassium tetrachloroplatinate, lignohumic acid ammonium salts, and an aqueous solution of sodium chloride.

2. The anticancer agent according to claim 1, wherein the potassium tetrachloroplatinate, lignohumic acid ammonium salts, and aqueous solution of sodium chloride are present in the following ratio:

| | |
|---|---|
| lignohumic acid ammonium salts | 0.18-0.22 mg |
| potassium tetrachloroplatinate | 0.020-0.040 mg |
| sodium chloride isotonic solution | 0.97-0.99 ml |
| distilled water | up to 1.0 ml. |

* * * * *